(12) United States Patent
Viovy et al.

(10) Patent No.: US 9,939,439 B2
(45) Date of Patent: Apr. 10, 2018

(54) MICROFLUIDIC SYSTEM HAVING A MAGNETIC PARTICLE BED

(71) Applicants: Jean-Louis Viovy, Paris (FR); Sanae Tabnaoui, Riehen (CH); Laurent Malaquin, Linas (FR); Stéphanie Descroix, Paris (FR)

(72) Inventors: Jean-Louis Viovy, Paris (FR); Sanae Tabnaoui, Riehen (CH); Laurent Malaquin, Linas (FR); Stéphanie Descroix, Paris (FR)

( * ) Notice: Subject to any disclaimer, the term of this patent is extended or adjusted under 35 U.S.C. 154(b) by 300 days.

(21) Appl. No.: 14/426,342

(22) PCT Filed: Sep. 6, 2013

(86) PCT No.: PCT/FR2013/052057
§ 371 (c)(1),
(2) Date: Mar. 5, 2015

(87) PCT Pub. No.: WO2014/037674
PCT Pub. Date: Mar. 13, 2014

(65) Prior Publication Data
US 2015/0219650 A1    Aug. 6, 2015

(30) Foreign Application Priority Data
Sep. 7, 2012    (FR) ...................... 12 58396

(51) Int. Cl.
*B03C 1/00*    (2006.01)
*G01N 33/569*    (2006.01)
(Continued)

(52) U.S. Cl.
CPC ....... *G01N 33/56966* (2013.01); *B03C 1/288* (2013.01); *G01N 33/54326* (2013.01);
(Continued)

(58) Field of Classification Search
CPC ............ B03C 2201/18; B03C 2201/22; G01N 33/54326; G01N 35/0098;
(Continued)

(56) References Cited

U.S. PATENT DOCUMENTS 7,309,439 B2    12/2007  Fernandez et al.
2011/0137018 A1*  6/2011  Chang-Yen ........ G01N 35/0098
                                                    530/412
(Continued)

FOREIGN PATENT DOCUMENTS

EP    1331035    7/2003
EP    1974821    10/2008
(Continued)

OTHER PUBLICATIONS

Written Opinion of the ISA for PCT/FR2013/052057, completed Nov. 4, 2013, 7 pages.*
(Continued)

*Primary Examiner* — Erik B Crawford
(74) *Attorney, Agent, or Firm* — Duane Morris LLP; Gregory M. Lefkowitz; Jason M. Nolan

(57) ABSTRACT

The invention concerns a microfluidic system (1) comprising:
  at least one channel (2) for the flow of fluid having an inlet (4), an outlet (5) and a longitudinal axis (7) extending between the inlet (4) and the outlet (5), said channel (2) comprising a capture zone (3), and the cross section of the channel (2) orthogonal to the longitudinal axis (7) of the channel (2) increasing in size in the capture zone (3), from the inlet (4) towards the outlet (5) of the channel (2); and
  means (6) for applying a magnetic field having a decreasing intensity in the capture zone (3) of the channel (2), from the inlet (4) towards the outlet (5) of the channel.

The invention also concerns a method for treating a sample that can be implemented with this system.

11 Claims, 7 Drawing Sheets

(51) Int. Cl.
   *B03C 1/28* (2006.01)
   *G01N 33/543* (2006.01)
   *B03C 1/01* (2006.01)

(52) U.S. Cl.
   CPC .......... *G01N 33/56916* (2013.01); *B03C 1/01* (2013.01); *B03C 2201/18* (2013.01); *B03C 2201/26* (2013.01); *G01N 2333/255* (2013.01); *G01N 2333/70596* (2013.01)

(58) Field of Classification Search
   CPC ......... B01L 2400/043; B01L 3/502761; B01L 2200/0647; B01L 2200/0668
   See application file for complete search history.

(56) References Cited

U.S. PATENT DOCUMENTS

| | | |
|---|---|---|
| 2011/0212440 A1 | 9/2011 | Viovy et al. |
| 2013/0143234 A1 | 6/2013 | Inaba et al. |

FOREIGN PATENT DOCUMENTS

| | | | |
|---|---|---|---|
| WO | 1998023379 | 6/1998 | |
| WO | 2010041230 | 4/2010 | |
| WO | WO 2011155489 A1 * | 12/2011 | ............. B03C 1/033 |

OTHER PUBLICATIONS

Beyor N, Seo T S, Liu P, Mathies R A (2008) Immunomagnetic bead-based cell concentration microdevice for dilute pathogen detection. Biomed Microdevices 10 (6):909-917. doi:Doi 10.1007/S10544-008-9206-3.

Gijs M A M, Lacharme F, Lehmann U (2010) Microfluidic Applications of Magnetic Particles for Biological Analysis and Catalysis. Chem Rev 110 (3):1518-1563.

Seibert, K. D. And Burns, M. A. (1998), Effect of Hydrodynamic and Magnetic Stabilization on Fluidized-Bed Adsorption. Biotechnol Progress, 14: 749-755. doi: 10.1021/bp980080z.

Tong, X.-D. and Sun, Y. (2003), Application of Magnetic Agarose Support in Liquid Magnetically Stabilized Fluidized Bed for Protein Adsorption. Biotechnol Progress, 19: 1721-1727. doi: 10.1021/bp030028p.

Yasui, T, Mohamadi, M.R., Kaji, N., Okamoto, Y., Tokeshi, M., Baba, Y. (2011). Characterization of low viscosity polymer solutions for microchip electrophoresis of non-denatured proteins on plastic chips. Biomicrofluidics, VO 5. IS 4. SP 044114OP. doi:10.1063/1.3668233.

* cited by examiner

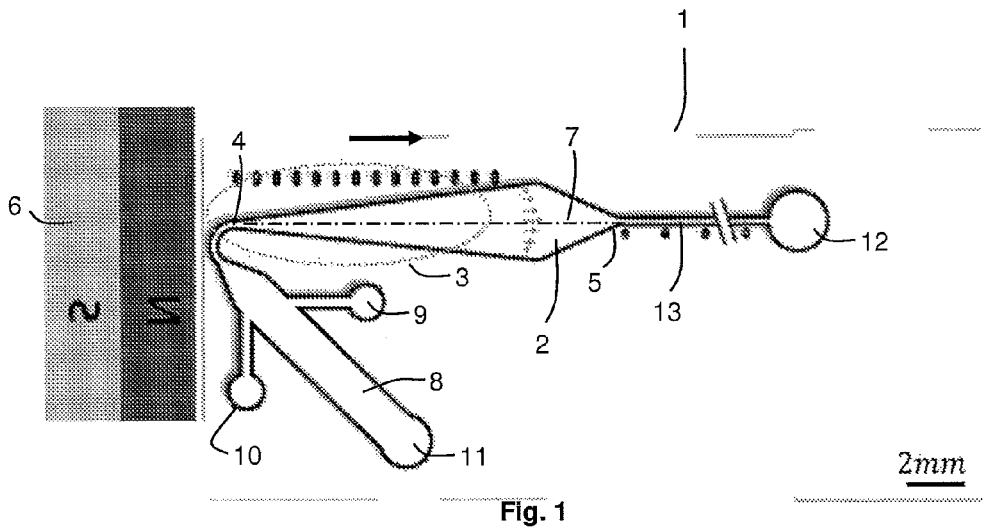
Fig. 1
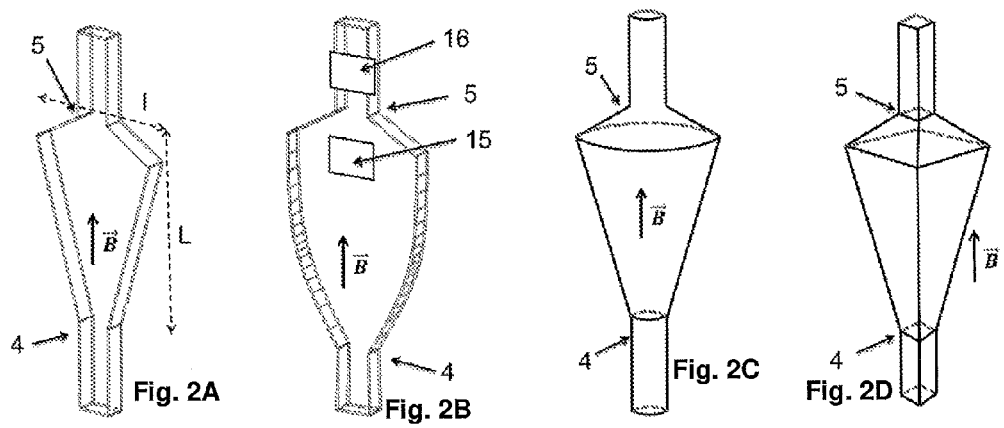
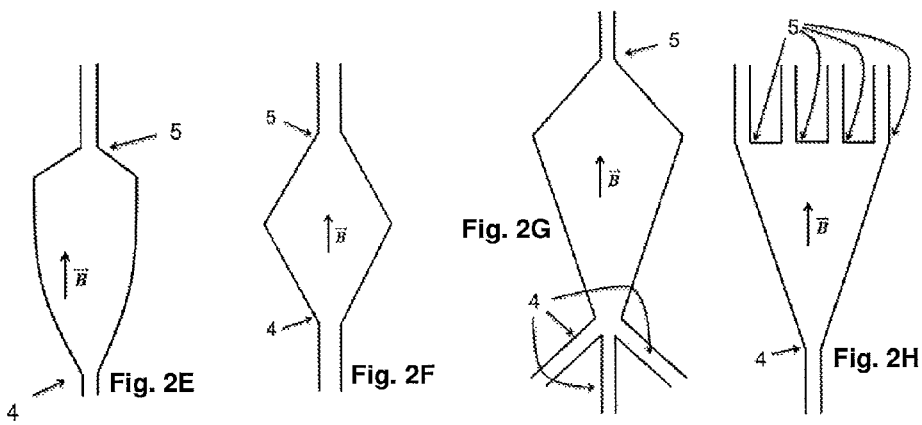

MICROFLUIDIC SYSTEM HAVING A MAGNETIC PARTICLE BED

CROSS-REFERENCE TO RELATED APPLICATIONS

This application is a § 371 national stage entry of International Application No. PCT/FR2013/052057, filed Sep. 6, 2013, which claims priority to French Patent Application No. 12/58396, filed Sep. 7, 2012, the entire contents of which are incorporated herein by reference.

FIELD OF THE INVENTION

The present invention concerns a microfluidic system having a magnetic particle bed, as well as an analysis method based on the use of this system.

TECHNICAL BACKGROUND

Microfluidic systems make it possible to manipulate small volumes of fluid, up to less than 1 microliter. They have thus opened the way to novel applications in biology, chemistry or physics that are impossible to implement successfully with conventional systems.

These systems make it possible for example to carry out analyses to the scale of individual molecules or individual cells and to perform biochemical reactions in very small volumes, greatly increasing the dynamics and reliability of the reactions: polymerisation chain reactions (PCRs) to the scale of an individual DNA molecule and new generation sequencing technologies are examples of such analyses.

On a macroscopic scale, performing purification, extraction and concentration operations by means of a solid phase is known, in particular in the context of chromatographic or immunoaffinity applications. However, using chromatographic separation microcolumns in microfluidic systems poses serious problems in terms of homogeneity of the microcolumns; furthermore, high pressures are necessary for circulating fluids in microfluidic systems, and the micromanufacture of systems with complex shapes may be laborious.

The use of magnetic particles, and in particular superparamagnetic particles, as the solid phase in microscopic-scale systems has enjoyed a certain degree of popularity. This is because magnetic particles bonded to an analyte of interest may be retained by a magnet while the surrounding fluid is eliminated. Methods of this type may be multiplexed, for example using multiple magnets disposed at the bottom of microtitration plates. Such systems do however have the drawback of limitations for example vis-à-vis the reaction speed, relatively high necessary elution volumes and a mediocre efficacy of mixing and rinsing.

Using superparamagnetic particles in microfluidic systems may make it possible to solve these problems: this is because the surface area/volume ratio is then high and the possibilities of functionalisation of the surfaces are numerous, while the magnetic properties of the particles afford easy contactless manipulation and make it possible to form compact structures such as microcolumns.

One challenge posed by methods of detection on chips is that of the concentration of the analytes in the analysis volume, or on the detection surface, to a level that must be sufficiently high vis-à-vis the detection threshold. It is therefore desirable to concentrate the samples before detection, which is tricky to achieve. This challenge is particularly great in the case of diagnostic applications, in which biological markers may be present at a very low concentration. For a typical microfluidic system functioning with a sample volume of 1 microliter or less, a step of pre-concentration from a larger volume (for example several milliliters) may be necessary.

Document WO 98/23379 describes a device for separating particles or molecules by migration through a ferrofluid. A magnetic field is applied perpendicular to the direction of movement of species to be separated, in order to create regions rich in or depleted of magnetic particles.

Document EP 1331035 describes an apparatus for retaining magnetic particles in a fluid-circulation cell. The cell is placed between the poles of a magnet, and high local gradients of a magnetic field are generated by means of microstructures present at the surface of the poles of the magnet. It is these high gradients that immobilise the magnetic particles.

Document EP 1974821 describes a system in which magnetic particles can be moved along a channel by a succession of electromagnets facing each other on either side of the lateral walls of the channel.

Document U.S. Pat. No. 7,309,439 describes a device for transporting magnetic particles in a capillary tube by means of magnetic devices placed around the tube.

The article by Beyor et al. in *Biomed. Microdevices* 10:909-917 (2008) describes a system using magnetic particles for detecting pathogenic agents on chips. A movable magnet is placed under a microchannel comprising bifurcations, which creates a compact barrier of particles that can be moved.

The article by Gijs et al. in *Chem. Rev.* 110:1518 (2010) is a review of the microfluidic applications of magnetic particles for biological analysis and catalysis. In particular, it is disclosed that magnetic particles can be retained and manipulated in microsystems by means of fixed or movable magnets or electromagnets placed on one side of a channel (below) or facing each other on either side of the channel (above and below).

Document WO 2010/041231 also describes a system in which magnetic particles are immobilised by means of a magnetic field transverse to the direction of flow.

Document WO 2010/041230 describes a microfluidic device for detecting analytes. The device comprises a microchannel and magnets disposed on either side of the microchannel and oriented so that a magnetic field essentially colinear with the direction of flow in the microchannel is generated. This system also makes it possible to create a plug of magnetic particles in a region of the microchannel. It is not suitable for use at relatively high rates.

Finally, it should be noted that systems proposing a circulation of fluid through combinations of magnetic and non-magnetic particles have been proposed.

Thus the article by Seibert et al. in *Biotechnol. Prog.* 14:749-755 (1998) describes a macroscopic system in which a series of annular coils are placed around a tube containing a fluidised bed for fermentation, containing magnetic and non-magnetic particles. The magnetic particles reduce the mixing effects in the bed.

The article by Tong et al. in *Biotechnol. Prog.* 19:1721-1727 (2003) describes another macroscopic system comprising a single coil around a fluidised bed creating a transverse field, which is used for increasing the compactness of the bed.

However, the latter two systems do not make it possible to process small volumes of fluid.

In summary of the above, the prior art proposes two types of microfluidic systems comprising magnetic particles. In the first type, the particles are organised in low-density static chains. The flow rate of fluid in this type of system may be relatively high because of the low density of the magnetic particles. However, the time taken for transporting the species of interest to the magnetic particles is high because of the large distances to be travelled. In the second type, the particles are organised in compact blocks, with generally regions where fluid circulates in the vicinity of the compact blocks. These compact blocks form plugs vis-à-vis the flow, so that the flow rate is limited.

There therefore exists a need to overcome the drawbacks of the systems of the prior art and in particular to have available a microfluidic system functioning at a relatively high flow rate, while ensuring good contact between the species of interest and the magnetic particles, that is to say a short time for the species of interest to diffuse towards the magnetic particles.

SUMMARY OF THE INVENTION

A first object of the invention concerns a microfluidic system comprising:
- at least one channel for the flow of fluid having an inlet, an outlet and a longitudinal axis extending between the inlet and the outlet, said channel comprising a capture zone, and the cross section of the channel orthogonal to the longitudinal axis of the channel increasing in size in the capture zone, from the inlet towards the outlet of the channel; and
- means for applying a magnetic field having a decreasing intensity in the capture zone of the channel, from the inlet towards the outlet of the channel.

According to one embodiment, the magnetic field applied in the capture zone is essentially parallel to the longitudinal axis of the channel.

According to one embodiment, the means for applying the magnetic fields comprise or consist of a magnet disposed outside the channel, preferably on the inlet side thereof.

According to one embodiment, the capture zone of the channel comprises magnetic particles, preferably superparamagnetic particles, the proportion by volume of these particles in the capture zone of the channel preferably being from 0.01 to 0.3.

According to one embodiment, the outlet of the channel is connected to a secondary conduit, the hydraulic resistance of which is greater than the hydraulic resistance of the channel, preferably by a factor greater than or equal to 2, or 5 or 10.

According to one embodiment, the system comprises means for moving fluid in order to effect the flow of fluid from the inlet to the outlet of the channel, and optionally a device suitable for generating oscillations of fluid in the channel, preferably chosen from sonic, ultrasonic or piezoelectric transducers, vibrating elements, loudspeakers and oscillating pistons.

A second object of the invention concerns a method for processing a sample, comprising a step of fluid flowing in a channel having a capture zone, the speed of flow of the fluid decreasing in the capture zone, and a magnetic field being applied in the capture zone, having decreasing intensity in the direction of flow of the fluid.

The method for processing a sample may in particular be a sample analysis method or for example a method for synthesis, chemical reaction, modification or separation of a sample.

According to one embodiment, during the step of fluid flowing, the magnetic field applied is essentially parallel to the mean direction of flow of the fluid in the capture zone.

According to one embodiment, during the step of fluid flowing, the capture zone contains magnetic, preferably superparamagnetic, particles, and the fluid flowing in the channel contains analytes; the method optionally comprising a supplementary step of detecting analytes and/or a supplementary step of collecting analytes downstream of the channel.

According to one embodiment, the method comprises the implementation of a chemical, biochemical and/or biological reaction and/or separation, preferably chosen from catalytic reactions, hybridisations, electrochemical reactions, enzymatic reactions, immunoassays, chromatographic separations, chemiluminescence reactions, immunological captures, affinity captures, elutions, purifications, concentrations, extractions and combinations thereof.

According to one embodiment, the method of the invention is implemented in the microfluidic system of the invention.

The present invention overcomes the drawbacks of the prior art. It provides more particularly a microfluidic system able to function at a relatively high rate, while ensuring good contact between the species of interest and the magnetic particles, that is to say a short time for diffusion of the species of interest towards the magnetic particles.

This is accomplished owing to the combination of a special channel shape, with a cross section increasing in the direction of flow of the fluid, and the application of a magnetic field decreasing in this direction of flow of fluid. In this way it is possible to retain magnetic particles in a zone of interest of the microchannel by equilibrium between the magnetic forces and the hydrodynamic forces applied.

Thus a region is available in which the magnetic particles both have a required density and preferably are not organised compactly, so as to allow a flow of fluid at a relatively fast rate, and are distributed relatively homogeneously in the fluid, thus ensuring optimum transport (and a minimum diffusion time) for the analytes of the fluid towards the magnetic particles.

The invention thus provides a fluidised bed of magnetic particles in a microchannel.

In a certain number of applications, the sensitivity of the microfluidic systems according to the invention is greater than that of the systems of the prior art.

The invention is particularly useful in the case where a step of concentration of analytes prior to detection is necessary (for example from a volume of a few milliliters up to a volume of a few microliters, or even less than one microliter).

Apart from the main features of the invention enumerated above, the method and system according to the invention may also have any one or more of the other features that follow.

According to one embodiment, the magnetic field in the capture zone of a channel does not have any local intensity peak or maximum.

According to one embodiment, the intensity of the magnetic field applied in the capture zone of a channel varies continuously, for example linearly, in the direction of flow.

According to one embodiment, the intensity of the magnetic field applied in the capture zone of the channel varies continuously, for example linearly, along the longitudinal axis of the channel.

According to one embodiment, the mean speed of the fluid (integrated over a transverse cross section of the channel, orthogonal to the longitudinal axis) in the capture zone of the channel varies continuously, in the direction of flow (or along the longitudinal axis of the channel).

According to one embodiment, the intensity of the magnetic field is greater at the inlet of the channel compared with the outlet of the channel.

According to one embodiment, the intensity of the magnetic field is greatest in the part of the capture zone that has the smallest transverse cross section.

According to one embodiment, the intensity of the magnetic field is smallest in the part of the capture zone that has the largest transverse cross section.

According to one embodiment, the transverse cross section of the capture zone increases continuously from the inlet to the outlet, and the intensity of the magnetic field of the capture zone decreases continuously from the inlet to the outlet.

According to one embodiment, the capture zone comprises magnetic particles, at least 50%, preferably at least 70% or at least 90% of the particles not being stacked compactly.

According to one embodiment, the capture zone comprises magnetic particles trapped in the capture zone, the magnetic particles undergoing continuous recirculation during the flow of a fluid from the inlet to the outlet of the channel.

According to one embodiment, the system according to the invention comprises a device for monitoring the difference in pressure between the inlet and outlet of the system and a flow meter for measuring the flow of fluid entering or leaving the capture zone, the pressure-monitoring device being able to adjust the pressure at the inlet of the channel or to adjust the difference in pressure between the inlet and outlet of the channel, according to the flow rate of fluid measured by the flow meter.

According to one embodiment, the method of the invention comprises a step of applying a predefined pressure at the inlet of the channel, while maintaining the magnetic particles in the capture zone in a compact stacking state.

A third object of the invention is a microfluidic system comprising a channel comprising a capture zone subjected to a magnetic field having an intensity gradient along the capture zone, a source of fluid connected to an inlet of the capture zone, and a secondary conduit connected to the channel upstream or downstream of the capture zone and having a hydraulic resistance greater than the hydraulic resistance of the capture zone of the channel (in the absence of any magnetic particles), preferably by a factor of at least two, or at least five, or at least ten, and for example ten to one hundred times greater.

According to one embodiment of this third object of the invention, the capture zone of the channel broadens in the principal direction of flow of fluid in the channel.

According to one embodiment of this third object of the invention, the system comprises magnetic equipment capable of producing a magnetic field oriented along the longitudinal axis of the channel in the capture zone, the intensity of the magnetic field decreasing (preferably continuously) in the capture zone.

A fourth object of the invention is a microfluidic system comprising:
  at least one channel for the flow of fluid having an inlet, an outlet and a longitudinal axis extending between the inlet and outlet, said channel having a capture zone;
  means for applying a magnetic field;
  wherein, in the capture zone of the channel:
    the cross section of the channel orthogonal to the longitudinal axis increases from the inlet towards the outlet of the channel;
    the magnetic field applied is essentially parallel to the longitudinal axis of the channel.

Associated therewith is an analysis method, comprising a step of fluid flowing in a channel having a capture zone, the speed of flow of the fluid decreasing in the capture zone, and a magnetic field being applied in the capture zone, essentially parallel to the direction of flow of the fluid.

A fifth object of the invention is a microfluidic system comprising a channel provided with an inlet and outlet, the channel broadening from the inlet in order to form a capture zone, and equipment for generating a magnetic field being disposed outside the channel, on the same side as the channel inlet (that is to say the inlet of the channel is the point on the channel closest to the equipment).

A sixth object of the invention is a microfluidic system comprising a fluidised bed of magnetic particles stabilised by a magnetic field in a capture zone of a channel, said magnetic field decreasing essentially monotonically from one end of the capture zone to the other.

In some embodiments, each of these third, fourth, fifth and sixth objects of the invention may also have the features described above in relation to the first object and the second object of the invention.

Another object of the invention is a method comprising the steps of:
  circulating a fluid containing magnetic particles in a channel comprising a capture zone having an expansion region, a magnetic field being applied in the capture zone, with an intensity decreasing in the direction of expansion of the channel, so as to retain the magnetic particles in the capture zone;
  circulating a fluid containing analytes in the channel, in the presence of the magnetic field, at a rate such that the magnetic particles are moving but remain in the capture zone;
  optionally, direct or indirect interaction of the analytes with the magnetic particles retained.

Advantageously, this method is a special embodiment of the analysis method according to the invention described above or implemented with a system according to the invention.

According to an embodiment of any of the methods according to the invention, the following successive steps are provided:
  providing a microfluidic system according to the invention;
  circulating in the microfluidic system a first fluid containing magnetic particles carrying ligands, or a combination of magnetic particles and other colloidal objects carrying ligands, the magnetic field being activated;
  optionally, rinsing;
  circulating in the microfluidic system a second fluid containing analytes;
  optionally, rinsing;
  eluting any analytes bonded to the ligands and retained in the capture zone of the channel by circulation of a third fluid in the microfluidic system.

According to an embodiment of any of the methods according to the invention, the following successive steps are provided:
  providing a microfluidic system according to the invention;
  circulating in the microfluidic system a first fluid containing magnetic particles bearing ligands, or a combination of magnetic particles and other colloidal objects bearing ligands, the magnetic field being activated;

optionally, rinsing;
circulating in the microfluidic system a second fluid containing analytes;
collecting the analytes at an outlet of the microfluidic system;
optionally, detecting the analytes collected, or additionally treating the collected analytes.

The above two embodiments may be combined, with an analyte bonding and then an elution and a detection.

According to an embodiment of any of the methods according to the invention, the following successive steps are provided:
providing a microfluidic system according to the invention;
circulating in the microfluidic system a first fluid containing magnetic particles bearing ligands, or a combination of magnetic particles and other colloidal objects bearing ligands, the magnetic field being activated;
optionally, rinsing;
circulating in the microfluidic system a second fluid containing analytes;
optionally, rinsing;
optionally, circulating a third fluid in the microfluidic system, preferably containing additional ligands;
optionally, rinsing;
injecting a substrate into the microfluidic system;
detecting the results of a reaction of said substrate.

As will be shown in more detail in the description of embodiments, and in some examples, in particular in relation to FIGS. 6A and 6B, the possibility of controlling the passage from a compact state to a non-compact dense state also confers original hydrodynamic characteristics on the devices according to the invention, in particular in terms of non-linear or threshold behaviour, or the possibility of obtaining a pressure drop which is independent of the flow rate. These devices may therefore be advantageous as devices for controlling, stopping, starting, modifying or regulating flows or pressures in a microfluidic system. This is because, as shown in the examples, in some embodiments, the channel, containing magnetic particles in the presence of a magnetic field, may transit between a state of high hydrodynamic resistance and a state of low hydrodynamic resistance, wherein said hydrodynamic resistance varies little according to the flow rate.

Thus another object of the invention in one of its aspects is a device for controlling flow or pressure in a microfluidic system, characterised in that it comprises:
at least one channel for the flow of fluid having an inlet, an outlet and a longitudinal axis extending between the inlet and the outlet, said channel comprising a capture zone, and the cross section of the channel orthogonal to the longitudinal axis of the channel increasing in the capture zone, from the inlet to the outlet of the channel;
magnetic particles in the capture zone of the channel; and
means for applying a magnetic field having a decreasing intensity in the capture zone of the channel, from the inlet towards the outlet of the channel.

BRIEF DESCRIPTION OF THE FIGURES

FIG. 1 schematically shows an embodiment of the microfluidic system according to the invention.

DESCRIPTION OF EMBODIMENTS OF THE INVENTION

Figure 2I:
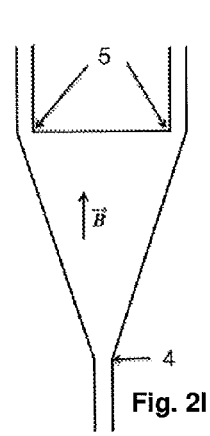
FIG. 2A to 2P schematically show various possible forms for the channel of a microfluidic system according to the invention.

The invention is now described in more detail and non-limitatively in the following non-limitative description.

Architecture of the Microfluidic System

The invention concerns a microfluidic system.

Microfluidic system preferably means a system comprising one or more microstructures on the surface of a substrate, which constitute elements suitable for containing and/or directing fluids. These microstructures have at least one dimension that is less than 5 mm, preferably less than 1 mm, and more particularly less than 500 µm. In some cases, these microstructures may have at least one dimension less than 200 µm, or 100 µm, or 50 µm or 20 µm, or 10 µm, or 5 µm, or 2 µm or 1 µm.

These microstructures may comprise closed volumes or in some cases have an open surface.

Channels (or microchannels) means microstructures suitable for the circulation/flow of fluids. They are usually closed over the whole of the travel of the fluids.

The substrate is preferably a plate or wafer. The substrate is preferably essentially rigid, which means that it can be manipulated and fixed so as to be held immobile, vis-à-vis a detector for example.

It may be made from glass, silicon, ceramic, metal or polymeric/plastics material. The substrate may be covered with a cover of the same nature, or a flexible material, such as silicone elastomer, for example polydimethylsiloxane.

Alternatively, the whole of the substrate and cover may be made from a flexible material, such as a silicone elastomer, for example polydimethylsiloxane.

The manufacture of the microstructures of the microfluidic system may be based on micromanufacture techniques such as film deposition, photolithography, etching (chemical or plasma), thermoforming, moulding, injection moulding and adhesive bonding techniques. The film deposition may be effected by centrifugation, thermal oxidation, chemical or physical vapour deposition (CVD and PVD), low-pressure CVD, plasma-enhanced CVD, sputtering, etc.

The microfluidic system may be or comprise a lab-on-a-chip.

The microfluidic system may comprise a network of channels, that is to say a plurality of channels disposed between the substrate and its cover, or entirely surrounded by the substrate, and which are in fluid communication either with each other or with one or more sources of fluid external to the system.

The microfluidic system may also comprise a series of channels, that is to say a set of a plurality of unconnected channels, or a network of unconnected channels, on the same substrate.

The microfluidic system may be connected to reservoirs of fluids or samples and other related devices by tubes or pipes or connectors (for example in a Y or X shape), in order to bring fluids to or collect fluids from the system. Alternatively, these tubes or pipes and optionally the reservoirs and other related devices may be considered to form part of the microfluidic system.

Referring to FIG. 1, a microfluidic system 1 according to the invention comprises at least one channel 2 for flow of a fluid with an inlet 4 and an outlet 5, as well as means for applying a magnetic field 6.

It may be in the form of an assembly comprising firstly the microfluidic device (a microstructured substrate comprising the channel, and the manifolds, reservoirs, and other elements in fluid connection therewith) and secondly the means for applying a magnetic field, not necessarily fixed or linked to the microfluidic device.

The terms inlet and outlet are chosen with reference to the majority direction of flow of a fluid containing analytes (in the presence of magnetic particles in the capture and magnetic-field zone, as described below). For the requirements of some protocols, it may however be necessary, transiently, to make some fluids flow in the opposite direction (from the outlet to the inlet), or between inlets and outlets different from those used for the circulation of the sample containing the analytes, for example for rinsing operations, while remaining within the scope of the invention.

The choice of the material for forming the channel is made according to the nature of the fluids to be transported, the shape of the channel and other elements of the microfluidic system, cost, ease of production, etc. The channel may in particular be made from glass, or other non-magnetic solids such as ceramic, or from polymer. The polymer may be an elastomer, such as polydimethylsiloxane, or a fluorinated polymer such as those known by the name "Dyneon". A thermoplastic polymer could also be used, such as an olefin polymer or copolymer, in particular cyclic olefin, polycarbonate, polymethyl methacrylate, polystyrene or polyethylene terephthalate. Transparent polymers are preferred, optionally in combination with glass.

The channel may also comprise a plurality of inlets and/or a plurality of outlets, on the assumption that it is a branched channel.

Referring once again to FIG. 1, the channel 2 has a zone of interest referred to as the capture zone 3, which is suitable for containing a bed of magnetic particles, and in particular a fluidised bed (or what is analogous to a fluidised bed on the scale of a microfluidic system) of magnetic particles.

The channel 1 has general elongate shape, with a longitudinal axis 7 between the inlet 4 and outlet 5.

Figure 2J:
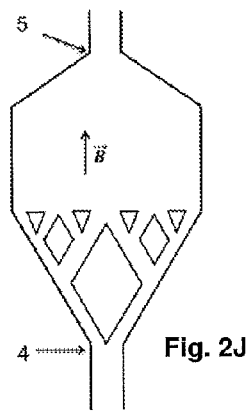
Figure 2K:
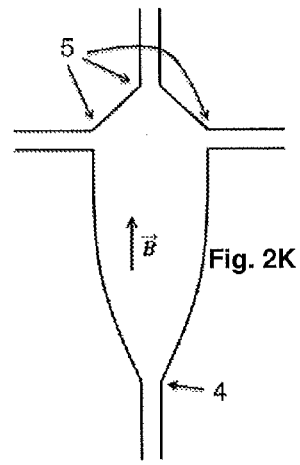
Figure 2L:
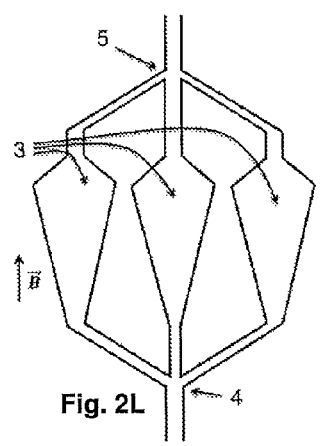
Figure 2M:
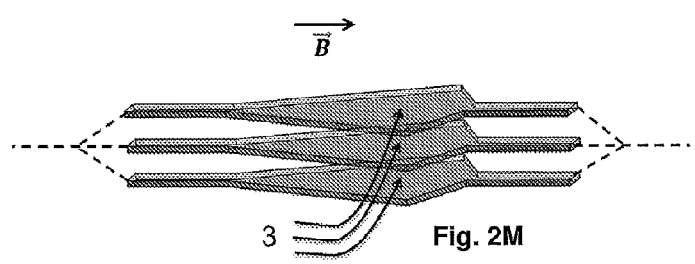
Figure 2N:
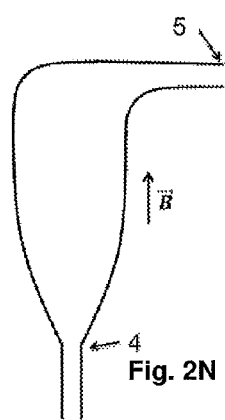

The longitudinal axis 7 is generally a straight line (at least in the capture zone 3 of the channel 2), as illustrated for example in FIG. 1, but it may in some cases be composed of segments of straight lines or be curved in the case where the channel comprises elbows or bends or changes in direction (for example FIG. 2N).

The longitudinal axis 7 of the channel 2 generally corresponds to the mean direction of flow of the fluid in the channel (which may be defined as the direction of the mean velocity vector of the fluid in the channel, in non-turbulent flow mode).

The longitudinal axis 7 may be an axis of symmetry of the channel 2, or at least of the part of the channel 2 forming the capture zone 3; or alternatively it may not be an axis of symmetry.

The transverse cross section of the channel is defined as being the cross section orthogonal to the longitudinal axis 7 of the channel 2.

It is preferred for the transverse cross section of the channel 2 at every point to be greater than or equal to (preferably greater than) the transverse cross section of the inlet 4 of the channel; and/or for the transverse cross section of the channel 2 at every point to be greater than or equal to (preferably greater than) the transverse cross section at the outlet 5 of the channel 2.

According to the invention, the capture zone 3 has the particularity of broadening along the longitudinal axis 7, in the direction of flow, that is to say the transverse cross section of the channel 2 increases along the longitudinal axis 7 from the inlet 4 towards the outlet 5 of the channel 2 (that is to say in the direction of flow).

For example, the channel may have a conical shape along its longitudinal axis. Alternatively, and preferably for greater simplicity of manufacture, the channel may have a rectangular transverse cross section, having a height (or thickness, in the direction perpendicular to the plane of the substrate) and a width, the width increasing in the direction of flow (the height remaining constant), or the height increasing in the direction of flow (the width remaining constant), or the width and height increasing in the direction of flow.

The channel advantageously has a constant height (thickness) for greater simplicity of manufacture.

In general terms, the channel may have a circular, oval, triangular, square, rectangular or other transverse cross section (including different forms at different positions along the longitudinal axis), and it may constitute a closed space or be open on one side towards the external environment (the top side), and this over the entire length of the channel or only part thereof. The channel may also, preferably, be closed, with the exception of the inlet and outlet.

The channel may be a capillary channel.

The increase in the transverse cross section is preferably continuous, and for example linear.

Downstream of the capture zone of the channel, the channel may comprise a downstream zone, which is therefore situated between the capture zone and the outlet. This downstream zone may have a constant or increasing transverse cross section, but also, preferably, a transverse cross section decreasing towards the outlet, in order to provide the necessary transition towards the outlet, which generally has a reduced dimension.

Preferentially, the capture zone has a generally elongate form. Preferentially, the whole of the channel has a generally elongate form.

Preferentially, the length of the channel, and/or the length of the capture zone, is greater than the maximum dimension of the channel in its transverse cross section, and in particular by a factor of at least 2, or at least 3 or at least 5, and which may range up to 20, 100 or 500.

The capture zone may in some cases be branched, in which case the transverse cross section consists of the sum of the transverse cross sections of the various branches.

The maximum dimension of the transverse cross section may for example, depending on the embodiments, be less than or equal to 5 mm, or 2 mm, or 1 mm, or 500 µm, or 200 µm, or 100 µm, or 60 µm, or 50 µm, or 40 µm, or 30 µm or 20 µm, or 10 µm, or 3 µm, or 1 µm, or 300 nm, or 100 nm, or 30 nm, or 10 nm.

Furthermore, the ratio of the length of the capture zone (the dimension along the longitudinal axis) to the maximum dimension of the transverse cross section may for example be from 1 to 500, and preferentially 2 to 50, more particularly 3 to 5, 5 to 20 or more rarely 20 to 50.

The height or thickness of the channel may in general range from 1 µm to 5 mm, preferably from 10 µm to 100 µm or from 100 µm to 1 mm.

The capture zone of the channel may have a volume ranging up to 10 mL. It is however preferred for it to have a small volume, for example from 1 mL to 10 mL, or 100 µL to 1 mL, or 10 µL to 100 µL, or 1 µL to 10 µL, or 100 nL to 1 µL, or 10 nL to 100 nL, or even 1 nL to 10 nL. Volumes below 10 µL are preferred.

It may be appropriate for the channel, and in particular its capture zone, or a region of the channel situated downstream of the capture zone, to be closed on one of its sides by a transparent material having a thickness compatible with a high-resolution microscopic observation, forming a "window". The thickness of the window is preferably less than 500 µm, in particular less than 200 µm.

Figure 2O:
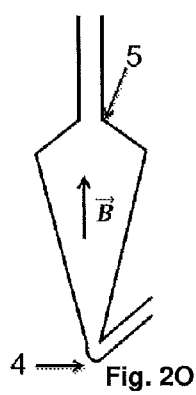
Figure 2P:
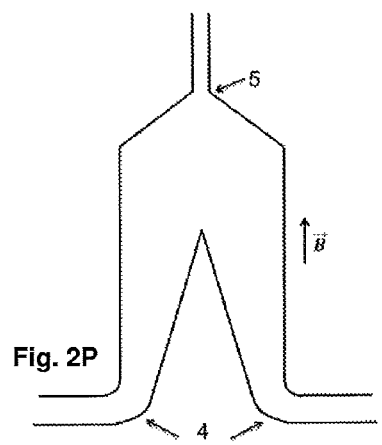

FIG. 2A to 2P illustrate various variants for the form of the channel described above, the inlet (or inlets) being referenced 4 and the outlet (or outlets) being referenced 5. The general direction of the magnetic field is illustrated by a vector on the diagrams.

FIG. 2A shows a channel with a single inlet 4 and a single outlet 5, a constant thickness, a length L, and a width I that increases linearly from a minimum at the inlet 4 to a maximum (less than the length L), and then decreases linearly to the outlet 5. The global form of the channel is therefore that of an asymmetric diamond. The capture zone 3 is situated between the inlet 4 and the region of the channel with the maximum width.

FIG. 2B shows a variant with a width that varies non-linearly. In addition, a window 15 (as described above) is provided on an upper or lower surface of the channel, and/or a window 16 is provided downstream of the channel.

FIG. 2C shows a variant in which the channel has a three-dimensional broadening, in the form of a cone.

FIG. 2D shows a variant in which the channel has a three-dimensional broadening, with a pyramidal form.

FIG. 2E shows a variant channel similar to that in FIG. 2B.

FIG. 2F shows a variant channel similar to that in FIG. 2A but with an essentially symmetrical diamond shape.

FIG. 2G shows a variant with an inlet 4 branched in three supply channels, upstream of the channel.

FIG. 2H shows a variant with four outlets 5, emerging on parallel respective downstream channels. In this variant, the width of the channel increases continuously from the inlet 4 as far as the outlets 5, without passing through a maximum, and the form of the channel seen from above is therefore roughly triangular.

FIG. 2I shows a variant similar to that of FIG. 2H, with only two outlets 5.

FIG. 2J shows a variant with multiple branches downstream of the inlet 4, of the delta type.

FIG. 2K shows a variant with three outlets 5, emerging on downstream channels in divergent directions.

FIG. 2L shows a variant in which the channel is branched in three branches between the inlet 4 and the outlet 5, disposed parallel in the same plane of the substrate of the microfluidic system, each branch comprising a capture zone 3 (with broadening of the branch from the inlet 4 to the outlet 5).

FIG. 2M shows a variant in which the channel is branched in three branches between the inlet 4 and the outlet 5, superimposed in various thicknesses of the substrate of the microfluidic system, each branch comprising a capture zone 3 (with broadening of the branch from the inlet 4 to the outlet 5). This arrangement makes it possible in particular to increase the global flow rate of the system using a single form, keeping its characteristics.

FIG. 2N shows a variant with a channel forming an elbow at the outlet 5.

FIG. 2O shows a variant with a channel forming an elbow at the inlet 4.

FIG. 2P shows a variant with a channel comprising two inlets 4, the channel comprising two branches that join, and a single outlet 5 downstream of the junction point.

Application of the Magnetic Field

Referring once again to FIG. 1, the invention provides means for applying a magnetic field 6, the magnetic field applied being essentially parallel to the longitudinal axis 7 of the channel 2. In the figure, the orientation of the magnetic field is illustrated by an arrow.

In particular, the direction of the magnetic field at any point in the capture zone 3 of the channel 2 forms an angle of less than or equal to 20°, or 15°, or 10°, or 5°, with respect to the longitudinal axis 7 of the channel 2; or the direction of the magnetic field at any point of the capture zone 3 of the channel is parallel to the longitudinal axis 7 of the channel.

Alternatively, the mean vector of the magnetic field over a transverse cross section of the channel can be taken into consideration. This mean vector forms an angle of less than or equal to 20°, or 15°, or 10°, or 5° with the longitudinal axis of the channel, along the capture zone of the channel; or this mean vector is parallel to the longitudinal axis of the channel along the capture zone.

This alignment of the magnetic field on the shape of the channel is also represented in terms of alignment of the magnetic field with the flow of fluid.

Thus, according to preferred embodiments:

the direction of the magnetic field at any point in the capture zone of the channel forms an angle of less than or equal to 20°, or 15°, or 10°, or 5°, with respect to the velocity vector of the fluid in the channel at this point (in non-turbulent flow);

the mean vector of the magnetic field over a transverse cross section of the channel forms an angle of less than or equal to 20°, or 15°, or 10°, or 5° with respect to, or is parallel with, the mean velocity vector of the fluid over said transverse cross section, along the capture zone of the channel.

Another essentially equivalent way of defining the parallelism of the magnetic field with respect to the capture zone of the channel (to within a few divergences or small local or temporal variations) consists of making it necessary for the magnetic field lines in the capture zone of the channel to be essentially aligned with the hydrodynamic field lines in this capture zone (in non-turbulent flow), that is to say the angle between these respective field lines is less than or equal to 20°, or 15°, or 10°, or 5° at any point in the capture zone.

The component of the magnetic field in the plane of the substrate perpendicular to the longitudinal axis 7 of the channel 2 (lateral component) is at every point less than 30%, or 20% (or 15%, or 10%, or 5%) of the component of the field along the longitudinal axis, and the field is therefore oriented almost along the longitudinal axis 7 in the whole of the channel 2. It should be noted that the presence of a decrease in the field along the longitudinal axis results, by conservation of the flow, in a divergence of the field, and that, at some points, and in particular towards the walls of the channel, the field consequently has a non-zero lateral component.

This magnetic field may be created by means of a permanent magnet, an electromagnet, or a combination thereof, optionally in association with a pole piece formed with a soft magnetic material able to direct the field lines. Preferably, such a pole piece is devoid of any microstructure liable to create a plurality of local maxima of the magnetic field.

In the case of the use of an electromagnet without a core, for example an electrical coil, it is considered that the poles of the electromagnet are the two planes corresponding to the entry and exit of the magnetic flux in the coil.

Hereinafter, unless mentioned to the contrary, the permanent magnets and the electromagnets will be referred to by the generic term "magnet".

In some embodiments, the magnetic field may be activatable or adjustable. In particular, it is advantageous to be able to modify the intensity (amplitude) of the magnetic field without modifying its orientation (that is to say its direction, or the form of field lines).

The invention makes provision for disposing the magnet with its north/south polar axis essentially aligned with the longitudinal axis of the channel. It is preferred to dispose the magnet on the same side as the channel inlet. This differs from forms proposed in the prior art, where the magnets or electromagnets are disposed on either side of the channel or above and/or below the channel, that is to say in any event close to the walls of the channel essentially parallel to the direction of flow.

The face of the pole part or of the permanent magnet facing the capture chamber may, according to the embodiments implemented, be flat, or have various forms. For example, it may be curved in one or more directions, or even in some cases comprise one or more ridges. It is preferably configured so as to generate a field that decreases gradually and continuously inside the capture zone. If ridges exist, they must therefore preferably have an obtuse angle, preferably greater than 60°, or greater than 80°. Likewise, if said face of the pole part or of the magnet is curved and convex (arched), it preferably has a radius of curvature greater than the length of the portion of the capture zone intended to receive and retain magnetic particles. Adjusting the form of the pole piece (or other magnet) may make it possible to modulate the divergence of the magnetic field and therefore to optimise the performances of the system, according to the form of the channel and of its capture zone, either by trial and error or by digital simulation.

Thus the magnetic field provided in the invention preferably varies continuously and monotonically (in a decreasing fashion) along the longitudinal axis or the direction of flow, from the inlet to the outlet, in the capture zone. Any local intensity maximum, which could lead to local and therefore compact trapping of magnetic particles, is thus avoided.

Non-linear or even non-continuous variations in the transverse cross section of the channel, in the mean speed of flow of the fluid and in the intensity of the magnetic field are possible in some cases, depending on the required flow rates and residence times of the fluid.

Figure 9:
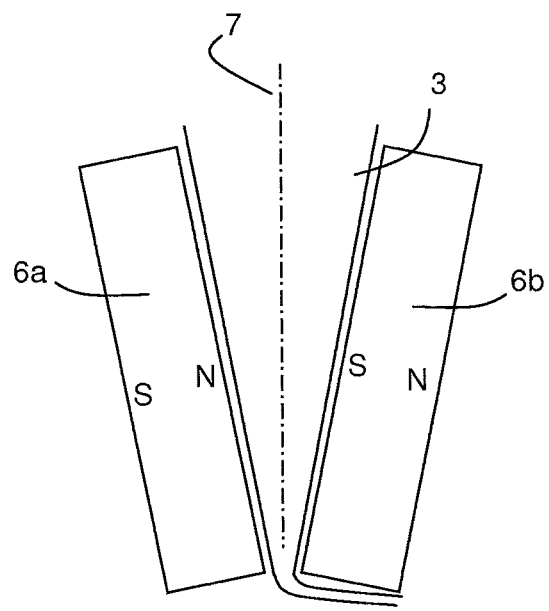
FIG. 9 shows schematically a detail of an embodiment of the microfluidic system according to the invention.

According to an alternative embodiment illustrated in FIG. 9, the magnetic field is essentially orthogonal to the longitudinal axis 7 of the channel, instead of being essentially parallel. For example, the means of applying a magnetic field 6 may comprise a first magnet 6a and a second magnet 6b situated on either side of the capture zone 3 of the channel and facing each other, the north pole of the first magnet 6a being directed towards the channel, and the south pole of the second magnet 6b being directed towards the channel.

The face of the north pole of the first magnet 6a is not parallel to the face of the south pole of the second magnet 6b, so that the intensity of the magnetic field decreases in the capture zone 3 in the direction of flow (the faces of the magnets are closer to the upstream side than to the downstream side in the capture zone 3).

In the example illustrated, the capture zone 3 is delimited by non-parallel sides of the channel that separate in the direction of the flow, and the magnets 6a and 6b are disposed parallel to these sides of the channel.

Magnetic Particle Bed

The arrangement described above makes it possible to form a magnetic particle bed in the capture zone of the channel. More precisely, a fluid containing magnetic particles is injected into the channel and the magnetic field is applied simultaneously (or after the start of the injection of the fluid containing the magnetic particles).

By correctly adjusting the intensity of the magnetic field and the flow rate of fluid, equilibrium is achieved between the magnetic and hydrodynamic forces, retaining the magnetic particles in the capture zone. It is then possible to introduce other fluids into the channel, devoid of magnetic particles, and to pass them through the magnetic particle bed retained in the capture zone.

Preferably, the magnetic particle bed in the system is a dense but non-compact bed. Thus the particles move relative to one another.

A compact state is defined as a state in which the particles are in permanent or almost permanent contact with the adjacent particles. A dense but non-compact state is a state in which the particles come into contact with one another occasionally, but in which the particles are preponderantly in contact with the fluid rather than with other particles (the mean distance between particles however preferably being less than 100 times, or 50 times, or 20 times, or 15 times, or 10 times, or 5 times, or 3 times less than the mean size of the particles).

Thus the dense but non-compact state that is sought in the context of the invention generally corresponds, for spherical or approximately spherical particles, to a volume fraction occupied by the particles of 0.01 to 0.3 in the capture zone, for example 0.01 to 0.05 or alternatively 0.05 to 0.3. By way of comparison, a compact stack of spherical or approximately spherical particles generally corresponds to a volume fraction occupied by the particles of 0.4 to 0.6.

For non-spherical particles, and in particular for very elongate particles, the dense but non-compact state that is sought in the context of the invention may correspond to a lower volume fraction, for example 0.001 to 0.1, since these particles have a tendency to interact more easily with one another, and have more difficulty in achieving a compact state.

Reference can also be made to the porosity of the magnetic particle bed, which is defined as being the volume fraction not occupied by the magnetic particles. This porosity of the magnetic particle bed is equal for example to 50% to 95%, or preferably 60% to 90%.

In some embodiments of the methods of the invention, in certain steps the capture zone comprises a dense but non-compact bed of magnetic particles, as described above, and in other steps it comprises a compact bed of magnetic particles as described above (with for example an occupied volume fraction of 0.4 to 0.6), the change from one regime to the other being able to be made by adjusting the flow rate, the pressure or the magnetic field.

Supplementary Means Associated with the Channel of the Microfluidic System

The system according to the invention comprises a set of means for ensuring the injection and controlled circulation of fluids in the channel.

Thus this system may comprise a plurality of other channels, additional inlets and outlets, and valves, as well as reservoirs for the various fluids used.

In the example illustrated in FIG. 1, the microfluidic system 1 comprises a supply channel 8 fluidically connected to the inlet 4 of the channel 2 described above. This supply channel 8 comprises a first inlet 9, a second inlet 10 and a third inlet 11, each of these inlets being able to be connected to a distinct fluid reservoir and/or to pressure control means. To the outlet 5 of the channel 2 described above, a secondary conduit 13 is connected, itself connected to an outlet 12 that may be connected to a fluid reservoir and/or to pressure control means.

In the example illustrated, the supply channel 8 forms an elbow with an angle greater than 90° with the main channel 2, which may be advantageous for bringing magnetic particles from a reservoir as far as the channel 2.

The regular character of the curvature, combined with the small cross section of the channel in this zone in which the magnetic field is not directed along the axis of the channel, and which therefore does not have the character of a capture zone according to the invention, makes it possible to prevent some magnetic particles remaining trapped in this section of the channel, and on the contrary forces the major part, and in the most favourable cases all, of the magnetic particles contained in the channel to join the capture zone 3 and to remain therein. However, any other conformation, in particular in the alignment of the channel 2, is possible. Likewise, in the example illustrated, the secondary conduit 13 is aligned along the longitudinal axis 7 of the channel 2, but any other conformation is possible.

The system according to the invention advantageously comprises (or is connected to, generally by fluid conduits) detection means such as optical detection means (for example for detection by luminescence, fluorescence, phosphorescence, light absorption, diffraction, refractometry or plasmon resonance) or electrical detection means (for example for detection by impedance measurement, conductometry, electrochemistry or cyclic voltametry), or acoustic detection means, for example sensors based on piezoelectric materials such as quartz microbalances or surface-wave resonators.

The system may comprise or be connected to analysis devices, connectors or chemical reactors; for example to a mass spectrometer, to a nucleic acid amplification device, to a "DNA chip" or "protein chip" often referred to as a "microarray", to a nucleic acid sequencer, to an electrophoresis device, to a filter, to a mixer or the like.

The system according to the invention advantageously comprises fluid-movement means, capable of moving a plurality of fluids such as reagents, samples, rinsing solutions or colloidal solutions, in a controlled manner in the channel, and also coming from reservoirs, or to any collection or detection instruments. These fluid-movement means may comprise microfabricated pumps or external pumps, such as microfluidic control pumps, syringe pumps, peristaltic pumps, membrane pumps, piston pumps or rotary pumps.

Preferably, pumps without impulsion are used, such as pressure-controlled microfluidic pumps. Such systems avoid any problems of hysteresis that may be encountered with pumping systems based on volume control, such as syringe pumps. This is because in the latter each stoppage of the flow has a tendency to cause a compact stacking of magnetic particles towards the inlet of the channel, blocking the inlet of the channel, and may lead to accumulation of pressure, then to a bursting of the compact stack of particles and to the loss of particles when the flow is re-established.

Pressure-control microfluidic pumps, such as for example the MFCS system from Fluigent, or the Mythos pump from Dolomite, avoid accumulating an excessive pressure and limit the above risks.

It is also preferred to use systems in which the pressure is regulated dynamically by means of information coming from a flow meter. This may make it possible for it to gradually increase the pressure in order to quickly increase or decrease the fluid flow rate through the magnetic particle bed in order to keep the flow rate within predetermined limits and thus avoid any phenomenon of bursting of the particle bed.

This is because, with this embodiment, it is possible to stop the flow, or reduce the flow rate to a low value, while preserving the magnetic field, and apply a finite controlled positive pressure to the inlet of the channel. Thus the magnetic particles are prevented from moving back in the region of the channel situated upstream of the capture zone.

In general the flow rate values with which the magnetic particles are in a compact state are 5 to 50 times, or even up to 500 times less compared with the flow rate values with which the magnetic particle bed is in a dense but non-compact state.

The microfluidic system of the invention may also be associated with, or may comprise, any data-processing, electronic or electrical controller, in order for example to control the temperature and functioning of the various components, to automate the operations and to record data.

In the context of the methods that can be implemented according to the invention, fluids are circulated in the microfluidic system, and in particular in the channel described above. The methods may comprise periods of continuous circulation of fluid, in alternation with periods of stoppage of fluid (which may in particular allow incubation and reaction steps). They may comprise periods of circulation of fluid at a first flow rate, in alternation with periods of circulation of fluid at a second flow rate that is preferably at least 10 times or at least 50 times less than the first flow rate.

Flow rates that may be used are in particular from 1 nL/min to 10 mL/min, and in particular 1 µL/min to 100 µL/min.

It is particularly advantageous to implement the invention in a mode of injecting fluid at the inlet of the microfluidic system and collecting fluid at the outlet of the system.

Secondary Conduit with High Hydraulic Resistance

According to one embodiment, the system according to the invention comprises a secondary conduit having a hydraulic resistance greater than that of the aforementioned channel, either upstream (before the channel inlet) or downstream (after the channel outlet), in series with respect to the (main) channel described above. This embodiment affords better control of the flow in the channel.

In the example in FIG. 1, the secondary conduit 13 has a hydraulic resistance greater than that of the channel 2, through a judicious choice of its length and transverse cross section (which may for example be equal to, or less than or equal to, the transverse cross section of the channel 2 at its outlet 5).

Preferably the hydraulic resistance of the secondary conduit is at least twice, or at least 5 times, or at least 10 times, for example between 10 times and 100 times that of the capture zone of the channel described above (in the absence of magnetic particles).

The secondary conduit may be a secondary channel formed in the same substrate as the channel, or it may be a tube or pipe connected to the channel.

Oscillating Device

According to one embodiment, the system according to the invention comprises, apart from means for moving fluid from the inlet to the outlet, an oscillating device, that is to say a device able to generate oscillations of fluid in the channel (and in particular in all or part of the capture zone). The oscillating device may generate mechanical vibrations or pneumatic oscillations. It is preferably chosen from sonic, ultrasonic or piezoelectric transducers, vibrating elements (in particular rotary or alternating motors connected to a mass), loudspeakers and oscillating pistons. The oscillating device may cause temporary reversals of the flow.

The oscillations thus generated may for example have a frequency of 1 Hz to 10 MHz, for example 2 Hz to 2 kHz, in particular 2 to 20 Hz, or 20 Hz to 200 Hz, or 200 Hz to 2 kHz. A range of 10 Hz to 1 kHz is preferred.

The oscillating device makes it possible to obtain a circulation of magnetic particles that is more homogeneous, and to increase the efficacy of the transport of the analytes towards the magnetic particles.

In the case where the oscillating device generates mechanical vibrations, it may be placed in direct sonic or mechanical communication with the channel, either by fixing it directly to the channel or to its support (optionally by means of a rod or other structure conducting the audible vibrations); alternatively it may be fixed to a flexible tube or pipe in fluidic communication with the channel (in particular a tube supplying or connecting fluid).

As shown in the examples below, an oscillating device makes it possible in some cases, and in particular when the particles have a tendency to aggregate because of their nature or because of the fluid in which they are contained, to improve the stability of flow and homogeneity of the magnetic particle bed. It also makes it possible in some cases to increase the flow, and to reduce the operating threshold pressure.

Fluids Treated According to the Invention

Some fluids used in the context of the invention are preferably colloidal suspensions, that is to say fluids containing colloidal objects.

Colloidal objects means organic or inorganic compounds, either natural or artificial, such as cells, organelles, viruses, aggregates of cells, islands of cells, embryos, pollen grains, natural or artificial organic particles (for example made from polymer latex), dendrimers, vesicles, magnetic particles, quantum dots, metallic particles, organometallic particles, metal oxide particles, ceramic particles, silica particles, glass particles, organic liquids, hydrogels, nanotubes, natural or artificial macromolecules, microgels, macromolecular aggregates, proteins or protein aggregates, polynucleotides or polynucleotide aggregates, nucleoprotein aggregates, polysaccharides, supramolecular assemblies or combinations of these.

The method of the invention is in particular implemented using at least one colloidal suspension of magnetic particles (microparticles or nanoparticles). These particles may be of various sizes, shapes and compositions. They may also be present in various distributions of size, shape and composition. The size of the particles is generally the mean mass dimension of the particles. For approximately spherical particles, this dimension corresponds to the diameter, and for non-spherical particles it corresponds to the maximum dimension.

Preferably, all or some of the magnetic particles are superparamagnetic particles. Such particles do not keep any permanent magnetic moment in the absence of an external magnetic field and can therefore move more easily with respect to one another, be preserved in a dispersed state, and be removed from the capture zone by modifying the magnetic field in this zone.

According to some embodiments, magnetic particles are used having a monomodal distribution with a size ranging from 10 nm to 100 µm, preferably from 100 nm to 10 µm.

According to other embodiments, magnetic particles are used having a bimodal or multimodal size distribution, with a first category of particles having a (mean) size ranging from 500 nm to 10 µm, and a second category of particles having a (mean) size ranging from 10 to 100 nm. It is also possible to use magnetic particles having a bimodal size distribution with a first category and a second category of particles, the (mean) size of the second category being 5 to 500 times less than the (mean) size of the first category.

Magnetic particles that can be used in the context of the invention are in particular those offered by Dynal, Miltenyi, Estapor, Polysciences, Ademtech and other companies. It is also possible to use magnetic particles synthesised ad hoc.

The invention also makes it possible to manipulate a combination of magnetic and non-magnetic particles.

In the context of the invention, samples of fluid are also manipulated, that is to say fluids containing analytes or substrates of interest. These may be body fluids, fluids extracted from a solid or liquid sample in which the analytes are initially present, or an artificial fluid such as a buffer, in which the analytes have been dissolved or suspended.

Analytes, Substrates and Ligands Treated or Used According to the Invention

The analytes or substrates may be any chemical or biological species, provided that they can be suspended or dissolved in a fluid. The analytes or substrates may be molecules, ions, atoms, macromolecules or colloidal objects (as defined above). They may be a single type of analyte or substrate or a plurality of types of analyte in a sample of fluid.

In general, the analytes or substrates referred to in the context of the present application are species that it is wished to separate from a sample of fluid, or to concentrate in this fluid, or to exchange from a first fluid to a second fluid, to examine them, analyse them, store them, identify them, cultivate them, use them for synthesis and/or to modify them chemically, biologically or physically.

Generally, the word "analyte" is used for species that it is wished to analyse without modifying them, and "substrate" for species that it is wished to modify, but in some applications species may in turn play the role of substrate and analyte, for example if it is necessary first to modify them in order to be able to detect them. Thus, in the description, the two words "analyte" and "substrate" can be substituted for each other while remaining in the scope of the invention.

Preferably, the magnetic particles used in the scope of the invention (able to be trapped in the capture zone of the channel) carry ligands on their surface.

Alternatively, or in addition, provision can be made for the ligands to be carried by other colloidal objects, themselves able to bond to the magnetic particles used in the scope of the invention (liable to be trapped in the capture zone of the channel).

The term ligand designates the species or a function able to bond reversibly or irreversibly to another species, in this case an analyte.

The ligands of the invention may be any chemical, physical or biological species able to fix to the surface of the magnetic particles (and possibly to other colloidal objects).

The analytes and ligands of the invention may for example be nucleic acids, polypeptides, amino acids, chemical compounds (or chemical functions with regard to ligands), enzymes or catalysts.

The term nucleic acid designates natural nucleic acids (for example DNA and RNA), but also modified or artificial nucleic acids such as block nucleic acids, peptide nucleic acids, thiolated nucleic acids, and others. It comprises genome, ribosome and mitochondrial nucleic acids, nucleic acids of pathogenic organisms, messenger RNA, microRNA and medicinal nucleic acids.

The term polypeptide is taken in its general sense and designates any molecule or molecular assembly comprising at least one sequence of amino acids, in particular natural and artificial proteins, protein fragments, protein complexes, enzymes, antibodies, glycopeptides, glycoproteins and chemical and biochemical modifications of these.

Ligands of particular interest for implementing the invention are antibodies, metals, hystidine, hydrophobic groups, hydrogen-bond groups, protein A, loaded nucleic acid sequences, polyelectrolytes, phospholipids, chemical compounds, medicines, fluorescent groups, luminescent groups, dyes, nanoparticles (in particular gold), quantum dots, DNA intercalating agents, aptamers, mixtures used for DNA amplification, and species able to affect the metabolism of cells or the properties (in particular the optical properties) of colloidal objects.

The bonding of ligands to analytes may be irreversible, which means that this bond cannot be broken without destroying or significantly altering the integrity of the analyte and/or of the magnetic particle (or other colloidal object). For example, it may be a covalent bond, or a bonding of denatured proteins on a surface, the irreversible attachment of latex on a surface by drying or communication of heat, etc.

The bonding of ligands to analytes may also be reversible, that is to say it may be broken without significantly modifying the species bonded. It may be in particular a bond of the physical type, or a bonding by hydrophobic or electrostatic or dielectrostatic interaction or by hydrogen interaction or by reversible chemical reaction.

A bonding by chemical interaction, for example by hybridisation of nucleic acid strands, by antigen-antibody interaction or by aptamer-protein interaction, may be reversible or irreversible.

As described above, the invention makes it possible to retain, in the capture zone of the channel, a magnetic particle bed, by applying the magnetic field (for a period greater than the residence time of the particles in the capture zone in the absence of a magnetic field). It is also possible to provide several capture zones along a channel or several channels in the microfluidic system. One of the advantages of the invention is that, although being retained in the capture zone or zones, the magnetic particles are however able to circulate inside this or these capture zones.

This magnetic particle bed is in its turn able to retain analytes circulating in the channel, either by direct bonding of the analytes to the magnetic particles or by indirect bonding of the analytes to the magnetic particles via other colloidal objects; or is able to react or interact in any way with these analytes (directly or indirectly, via other colloidal objects).

It is also possible to provide one or more steps of elution of the analytes retained in the capture zone, by injecting a suitable elution fluid.

It is also possible to use a second ligand, or supplementary ligand, which may be injected after a step (direct or indirect) of bonding the analytes to the magnetic particles in the capture zone, and which may advantageously facilitate the detection of the bonding of the analytes to the magnetic particles. There may for example be a secondary antibody, optionally bonded to a fluorophore, or optionally bonded to an enzyme. In this case, the ligand/analyte/supplementary ligand bonding may be detected by adding a substrate for the enzyme in question, for example a fluorogenic or chemiluminescent substrate.

Applications of the Invention

The invention makes it possible to implement, in the microfluidic system described above, chemical, biochemical or biological reactions or separations, such as in particular catalytic reactions, hybridisations, electrochemical reactions, enzymatic reactions, immunoassays, chromatographic separations, chemiluminescent reactions, immunological captures, affinity captures, elutions, purifications, concentrations, extractions and combinations of these.

According to several embodiments, the invention is implemented in the context of immunoassay methods, or genetic testing or ELISA testing.

According to some embodiments, the invention is implemented in the context of an analysis comprising a nucleic acid amplification, for example an isothermal amplification by PCR as described for example in A. Niemz et al., *Trends in Biotechnology*, May 2011, vol. 29, no. 5, p. 240-250.

According to some embodiments, the invention is implemented to carry out a chemical treatment of species contained in a fluid that is injected in the capture zone in the presence of magnetic particles.

The microfluidic system according to the invention may be associated with, or may comprise, any instrument for implementing the above embodiments, in particular any analysis, monitoring or production instrument, where applicable in the form of a miniaturised analysis system or a microreactor.

The invention may be implemented in the context of research, diagnosis, analysis, synthesis or quality control devices and methods, in medicine, biology, life sciences, the food industry, the cosmetics industry, pharmacy, legal analysis, safety, biosafety, the energy industry (in particular for handling radioactive materials) or chemistry.

The invention can make it possible to capture, sort, extract, purify, analyse, identify or cultivate analytes issuing from a sample of fluid.

The invention can make it possible to modify analytes contained in a fluid, for example by catalytic, chemical, biochemical or enzymatic reaction.

The invention can in particular make it possible to capture cells or viruses in a medium, to identify them or to lyse them. It may in particular be integrated in diagnostic devices and methods, in particular for the diagnosis of infectious illnesses, cancers, cardiovascular diseases, or prenatal diagnosis. It may also be integrated in devices and methods for quality control, or for controlling contaminations, in particular bacterial, viral or chemical, in the food, energy (particularly nuclear), water quality, chemistry, environment and safety (in particular bio-safety) fields.

The cells in question may be bacteria, moulds, eucaryotic cells, in particular circulating tumour cells, haematopoietic cells, red blood cells, circulating endothelial cells, parasites or circulating foetal cells.

EXAMPLES

The following examples illustrate the invention without limiting it.

Example 1—Hydrodynamic Field and Magnetic Field in the System According to the Invention A microfluidic system in accordance with FIG. 1 is produced. The channel 2 is 21 mm long and 50 μm thick, with a width varying from 100 μm to 2 mm (region of maximum width).

The microfluidic system is prepared with polydimethylsiloxane according to the microlithography protocol described in the article by Mohamadi et al. in *Biomicrofluidics*, 5,044114 (2011);

For generating the magnetic field, a permanent magnet of the NdFeB1 type is used, placed close to the channel 2: the distance between the magnet and the microfluidic system is 2 mm. The magnet is magnetised in its largest dimension and has a remanent magnetic field of 1.47 T. It has a size of 30×20×20 mm Simulations were carried out with 3D COMSOL in order to assess the intensity of the magnetic field in the channel 2 and the forces exerted on the magnetic particles.

Figure 3:
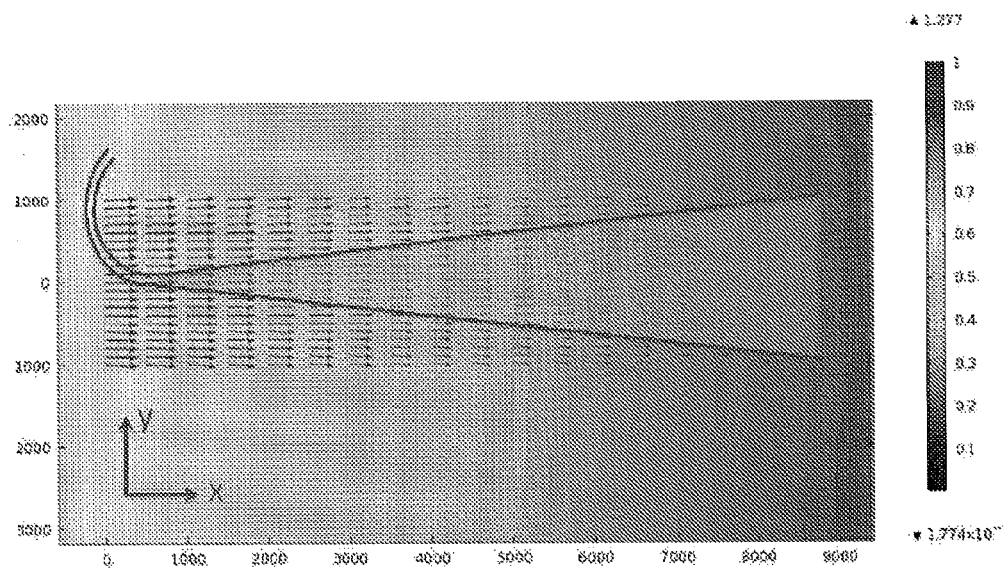
FIG. 3 is a magnetic field profile obtained in an embodiment of the invention (see example 1). The profile of the channel is shown superimposed on the representation of the magnetic field. The distance along the longitudinal axis of the channel is shown on the X-axis (in µm) and the distance along the width of the channel is shown on the Y-axis (in µm). The arrows represent the vectors of the magnetic field at each point, and the shade of the background represents the intensity of the magnetic field, according to the scale appearing on the right of the diagram (in tesla).
Figure 4:
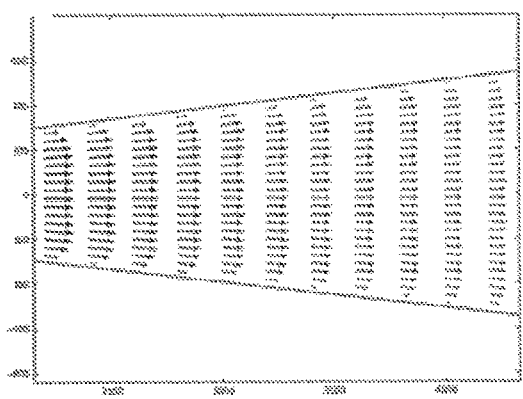
FIG. 4 shows a hydrodynamic field obtained in an embodiment of the invention (see example 1). The axes have the same meaning as for FIG. 3. The arrows represent the speed of the fluid at various points on the channel.

The results are shown in FIG. 3. It can be seen that the maximum intensity of the magnetic field is approximately 0.7 T at the inlet 4 of the channel 2. It decreases to 0.36 T at a distance of 1 mm.

The component of the magnetic field in the plane of the substrate perpendicular to the longitudinal axis 7 of the channel 2 (the lateral component) is small compared with the component of the field along the longitudinal axis, and the field is therefore oriented almost along the longitudinal axis 7 in the whole of the channel 2.

Knowing the intensity of the field at any point it is possible to calculate the magnetic force exerted on a magnetic particle, from the magnetic polarisability of this particle. In this example use was made of particles of the make DYNAL® at 2.8 μm.

Figure 5:
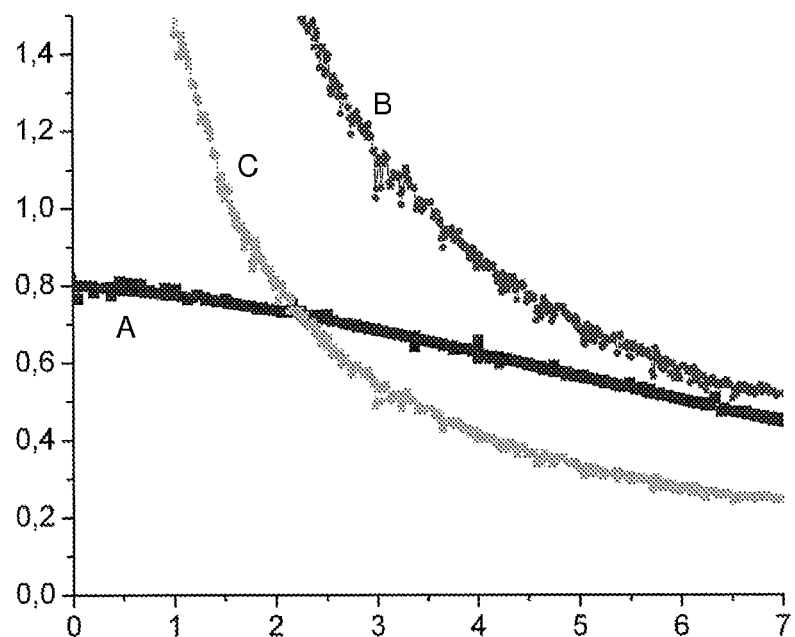
FIG. 5 shows the magnetic and hydrodynamic forces exerted on magnetic particles in an embodiment of the invention (see example 1). The X-axis is the distance along the longitudinal axis of the channel (in mm) and the Y-axis is the force in $10^{-10}$ N.

Likewise, using the COMSOL hydrodynamic library, the speed of flow for a given throughput was calculated at every point, in laminar mode (no Reynolds number). FIG. 5 provides an example of a hydrodynamic field calculated for a throughput of 3 μL/min.

The speed of the fluid decreases along the longitudinal axis, from 4.6 mm/s to 0.5 mm/s in 3 mm. The speed profile is almost flat in the transverse direction, the speed tending towards zero only in the immediate vicinity of the walls. In other words, the friction force exerted on the magnetic particles is almost uniform over the width of the channel (which is confirmed by experimental observation).

From the speed profile and the profile of the magnetic field, it is possible to calculate the magnetic and hydrodynamic forces exerted at any point on the channel, for a given flow and for an isolated particle.

The results are shown in FIG. 5. The curve A represents the magnetic force, the curve B represents the hydrodynamic force for a flow rate of 6 μL/min, and the curve C represents the hydrodynamic force for a flow rate of 3 μL/min.

It is deduced from this that, at a flow rate of 6 μL/min, the magnetic particles are entrained by the flow and are not trapped in the channel (because the hydrodynamic force is greater than the magnetic force at every point on the channel) but that, at a flow rate of 3 μL/min, there exists a stable equilibrium zone, that is to say a capture zone making it possible to retain the magnetic particles.

Thus, by relatively simple numeric simulations, it is possible to compute, for every channel shape and every magnet or pole piece shape, the hydrodynamic and magnetic force fields, and thus optimise the parameters of the system for a given type of particle and a given application (for example if a particular flow rate is required).

Example 2—Description of a Fluidised Bed of Magnetic Particles

The system of FIG. 1 is used, as well as, by way of comparison, the same system without the secondary conduit 13. The system is connected to a flow control device of the MAESFLO (Fluigent) type.

Figure 6A:
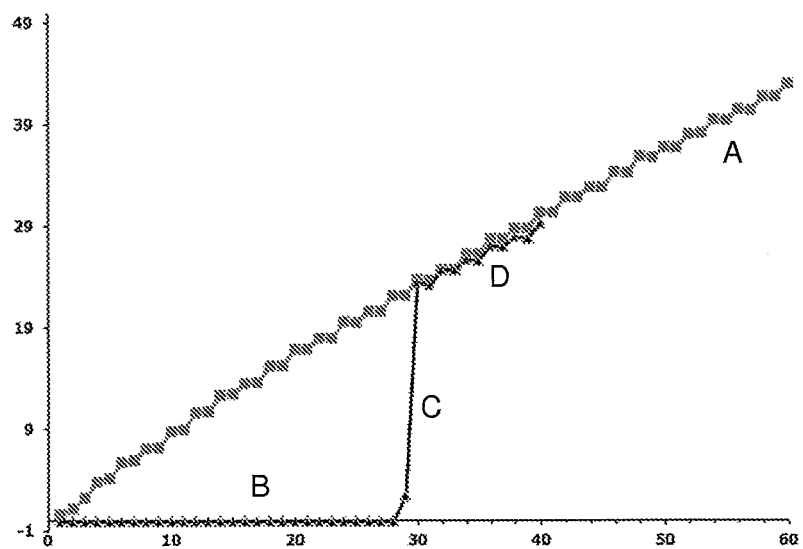
FIGS. 6A and 6B show the flow rate in microliters/min (on the Y-axis) as a function of the pressure in mbar (on the X-axis) in an embodiment of the invention (see example 2), respectively without a secondary conduit with a high hydraulic resistance downstream of the main channel, and with such a secondary conduit.

FIG. 6A illustrates the behaviour of the system (flow rate as a function of pressure) without the secondary conduit 13. Curve A is obtained in the absence of any magnetic particles. The channel 2 behaves as a simple hydraulic resistance, with a linear variation in the flow rate as a function of pressure.

The other curves are obtained in the presence of 50 μg of Dynabeads M-280 magnetic particles. By increasing the pressure from 0 to 30 mbar at a rate of 1 mbar/min (curve B), the flow rate remains below the detection threshold of the flow meter. The magnetic particles therefore obstruct the flow. This is confirmed by visual observation: it is found that the magnetic particle bed is in a compact state, the pressure being insufficient to compensate for the magnetic forces involved. Then, at approximately 30 mbar, there is a very rapid transient flow (curve C), and at a high pressure the flow rate regains the same value as in the absence of magnetic particles (curve D).

The system has therefore behaved like a threshold valve, which allows flow only above a threshold pressure.

Visual observation shows that, at the time of the jump, all the particles leave the channel: in the particular device used here, when the pressure capable of pushing the compact plug of magnetic particles against the magnetic field is exceeded, the transient flow created drives the particles from the channel.

Figure 6B:
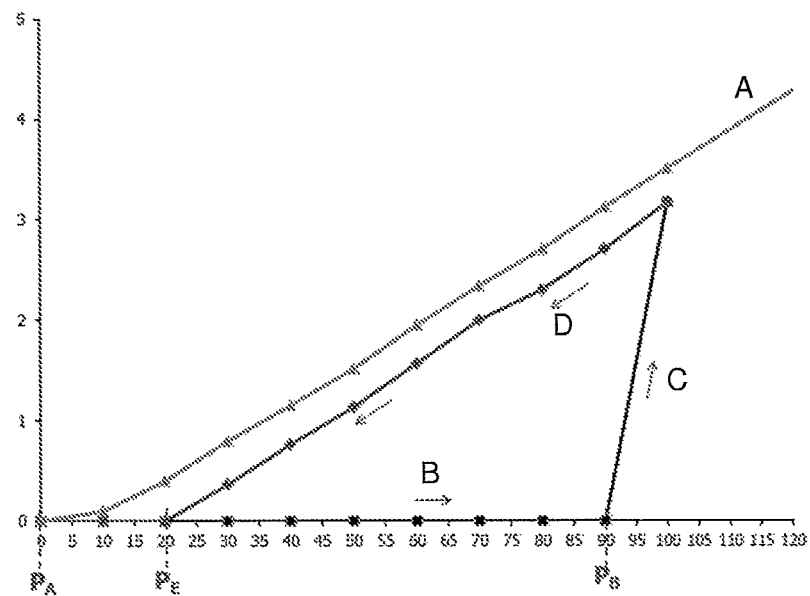

FIG. 6B illustrates the behaviour of the system (flow rate as a function of the pressure) when the secondary conduit 13 with a high hydraulic resistance is present. By way of (resistive) secondary conduit 13, use is made here of a tube made from polyetheretherketone (PEEK) with an inside diameter of 65 μm and a length of 8 cm. The hydraulic resistance of this tube is approximately $1.6 \times 10^{14}$ Pa·s·m$^{-3}$, whereas that of the channel 2 is approximately $2.4 \times 10^{13}$ Pa·s·m$^{-3}$.

Curve A is again obtained in the absence of magnetic particles. Curve B is obtained after introduction of 50 μg of Dynabeads M-280 particles, increasing the pressure from 0 mbar, at a rate of 1 mbar/min. Up to approximately 90 mbar, the flow rate remains below the detection threshold of the flow meter. The magnetic particles therefore obstruct the flow through their compact stacking (confirmed by visual observation).

Beyond a threshold situated at approximately 90 mbar, the magnetic particle bed expands, causing an increase in the flow rate up to approximately 3 µL/min (curve C). Beyond this threshold, the magnetic particle bed is in a fluidised state.

Unlike the previous case, when the pressure is reduced below the threshold of 90 mbar (curve D), the flow rate decreases in a gradual and affine fashion. This curve portion may be travelled reversibly. Under observation, it can be seen that the magnetic particles have remained in the capture zone and that none escape.

The system behaves here as a system that makes it possible to impose a difference in pressure that is constant and independent of the flow rate, between two points in a microfluidic system, here the inlet and outlet of the capture zone.

It should therefore be noted that the use of an outlet hydraulic resistance facilitates the use of the system and gives it novel flow or pressure control functionalities. However, it should be noted that other embodiments, in particular having more rigid connections, or other flow control modes, or other channel shapes, may not require such a hydraulic resistance via a secondary conduit.

Visual observation reveals that the apparent volume of the domain occupied by the magnetic particles increases very gradually when the flow rate is increased. It is also observed that this domain has a clearly defined extension in the channel 2, which increases with the flow rate, and remains relatively homogeneous.

This surprising discovery, different from all the systems of the prior art, constitutes a major advantage of the invention. It shares in fact certain advantages of fluidised beds which, in the prior art, require the use of gravity and much greater volumes. Moreover, because of the weakness of the gravitational force on micrometric particles, the fluidised beds of the prior art can be used mainly with gases, whereas in the invention it is also possible to work with liquids, which exert a much greater hydrodynamic friction.

By observing the extension of the domain of the channel 2 occupied by the magnetic particles according to the flow rate, it is possible to calculate the corresponding porosity of the magnetic particle bed.

The results were as follows:
Flow rate of 0 µL/min: porosity of 41%.
Flow rate of 0.5 µL/min: porosity of 66%.
Flow rate of 1 µL/min: porosity of 71%.
Flow rate of 1.5 µL/min: porosity of 75%.
Flow rate of 2 µL/min: porosity of 77%.
Flow rate of 2.5 µL/min: porosity of 79%.
Flow rate of 3 µL/min: porosity of 80%.
Flow rate of 3.5 µL/min: porosity of 81%.
Flow rate of 4 µL/min: porosity of 82%.

By way of comparison, the porosity of a compact system is generally between 40% and 60% (for spherical particles). It is therefore found that the invention offers a magnetic particle bed with a dense but non-compact configuration, which is favourable for optimising both the flow rate and the exchange between the particles and the medium.

Example 3—Immunoassay by Fluorescence

An immuno extraction is effected by means of 2.8 µm Dynabeads particles grafted with sheep IgG targeting rabbit IgG (supplier: Invitrogen). Experiments are carried out in a phosphate buffer (PBS) containing 0.1% bovine serum albumin (BSA) in order to limit non-specific adsorption. Two types of fluorescent marked IgG are used to evaluate the specificity of the test: Alexa Fluor® 488 anti-mouse rabbit IgG antibodies (target specific) and CD1a anti-human mouse monoclonal IgG1 antibodies (target non-specific). Use is made, as elution buffers, of a citrate buffer (0.1 M, pH 2-3), an ammonium buffer (0.16% ammonium) at pH 9 and a solution of 100 mM sodium dodecylsulphate (SDS).

The microfluidic system shown in FIG. 1 is used.

The immunoextraction method requires the sequential injection of various solutions into the system with a precise control of the volumes injected while avoiding the mixing of reagents. Use is made of a MAESFLO (Fluigent) system for controlling pressures, direct-acting solenoid valves and PEEK tubes between the reservoirs and the inlets of the system.

The first inlet 9 of the supply channel 8 is connected to an elution buffer reservoir (citrate buffer, pH 2).

The second inlet 10 of the supply channel 8 is connected to a reservoir of sample (either Alexa Fluor® 488 anti-mouse rabbit IgG or CD1a anti-human mouse monoclonal IgG1).

The third inlet 11 of the supply channel 8 is connected to a reservoir of rinsing buffer (PBS 1×, 0.1% BSA, pH 7.4).

The solutions are injected by applying a pressure of 45 mbar to the reservoir concerned with the pressure controller. The flow rate is measured with a flow meter integrated at the outlet of the device. A fluorescence detection window is provided in the secondary conduit 13.

The immunoextraction steps are as follows:
Rinsing of the magnetic particles.
Sample incubation.
Rinsing for recovering the non-bonded biomolecules.
Elution of the isolated targets.

Before any test, the microfluidic system is coated with an epoxy-dimethylacrylamide polymer in order to prevent the adsorption of particles and proteins on the surface of the channel. A 0.15% w/w solution of the polymer is injected just after oxidation of the channel by plasma. The polymer is incubated for 30 minutes and then rinsed with the rinsing buffer.

The system is prefilled with the rinsing buffer. The temperature is 20° C. during the entire experiment.

The marked IgG solution and the elution buffer are placed in their reservoirs.

The initial trapping of the magnetic particles is effected by disconnecting the first inlet 9 of the supply channel 8 from the controller and applying a pipette in order to inject 5 µL of magnetic particle suspension. The particles enter the system by sedimentation and are drawn by the magnetic field into the channel 2. Then the first inlet 9 is reconnected to the pressure controller and a pressure is applied to the first inlet 9 and to the third inlet 11.

A rinsing step is performed in order to balance the immunosupport.

Then the sample of solution containing the marked specific IgG (or the non-specific reference IgG) is infused at a rate of 1 µL/min (at 100 ng/mL). The non-bonded compounds are eliminated with rinsing with 20 µL of rinsing buffer at 2 µL/min.

Then an elution step is effected by injecting elution buffer.

In a first elution mode, 20 µL of buffer is injected at a rate of 0.5 µL/min.

In a second elution mode, 2 µL of buffer is injected at a rate of 0.5 µL/min (fluidised bed mode) and then the flow is stopped for 10 minutes, the immunosupport then being in compact stacking mode. This stoppage leaves more time for dissociation, improving the total yield of recovery of the target. The compactness of the bed also limits the dispersion of the target and improves the sensitivity of the test. Then the flow is reactivated for 2 minutes in order to release the targets.

The quantity of IgG eluted in the detection window is detected by measuring a fluorescence signal.

In order to facilitate restarting of the flow after the stoppage period, it should be noted that it is preferable to keep the bed of particles in a compact state, while maintaining between the inlet and outlet of the chamber a pressure difference that is finite but insufficient to depart from the compact state (P<PE in FIG. 6B).

The performances of these elution modes have been compared.

Figure 7A:
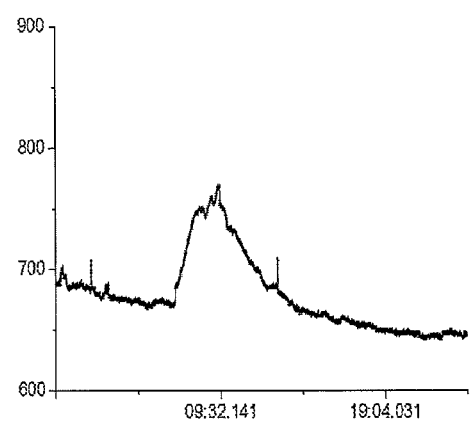
FIG. 7A to 7C show measurements of fluorescence obtained according to an embodiment of the invention (see example 3). The elution time appears on the Y-axis in minutes and the intensity of fluorescence appears on the Y-axis in arbitrary units.

FIG. 7A illustrates the elution peak obtained with the continuous elution mode (over 50 min). A wide band (6 min) is obtained with a height of 100 u.a. and a signal-to-noise ratio of approximately 20.

Figure 7B:
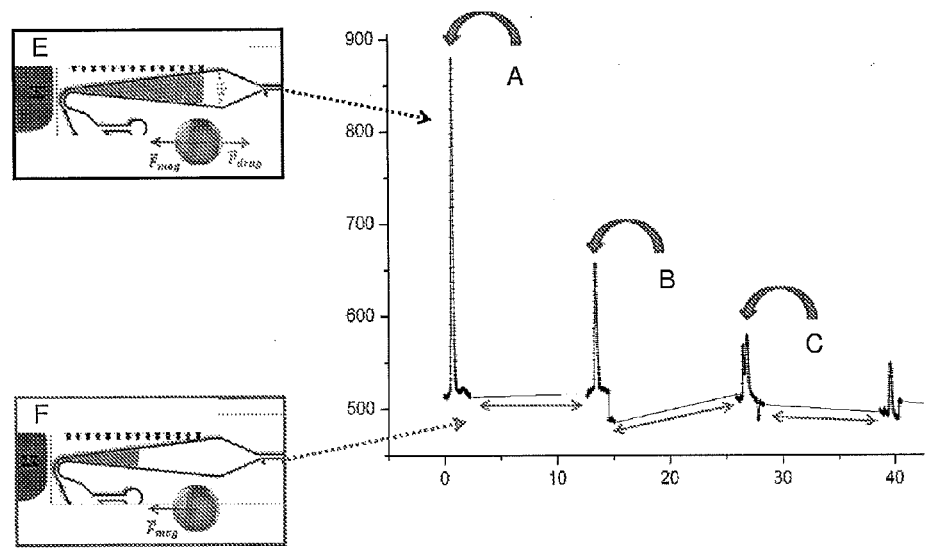

FIG. 7B illustrates the results with the alternating mode. Four successive elutions are carried out. On each occasion the fluorescence signal is measured for 2 minutes, with a latency time of 10 minutes. The elution peaks are more marked with this mode, with an intensity decreasing with the number of elutions.

The signal-to-noise ratio is improved by a factor of approximately 3.5 for the first elution compared with the first elution mode.

In the figure, the reference A corresponds to the first elution, the reference B to the second elution, the reference C to the third elution. On the left, E represents the extension of the magnetic particle bed in the channel when the fluid is circulating, and F is the extension of the magnetic particle bed in the channel when the circulation of fluid is stopped. The vectors $F_{mag}$ and $F_{drag}$ represent the magnetic force and the hydrodynamic force exerted on the particles.

The detection limit is tested by injecting 20 µL of marked IgG solution at 10 ng/mL, i.e. 0.2 ng of marked IgG. The alternate elution mode is used. A signal-to-noise ratio of approximately 7.5 and a detection limit of approximately 3 ng/mL are obtained.

Figure 7C:
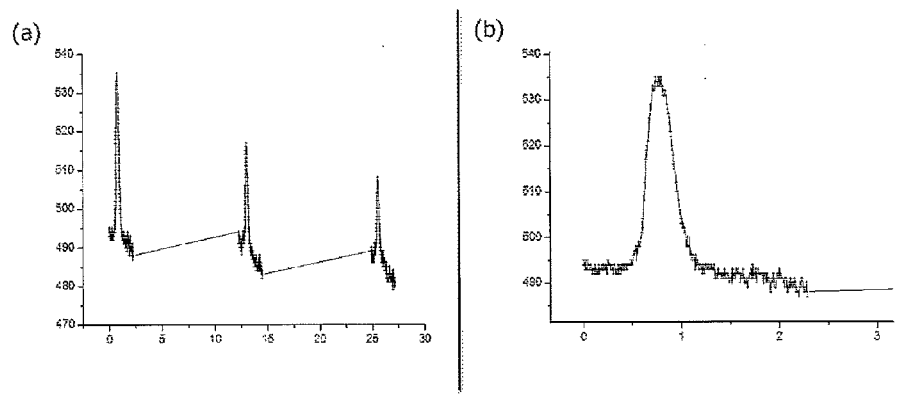

Finally, by injecting 200 µL of a 6 pM solution, the target is detected with a fluorescence signal-to-noise ratio of approximately 10: FIG. 7C. Part (b) of the figure shows a detail of part (a). By way of comparison, in the prior art, with similar magnetic particles and similar markers, the detection limit was 100 ng/mL: see Mohamadi et al. in *Biomicrofluidics* 5,044114 (2011).

Example 4—Oscillating Device

An experiment similar to that of example 2 is carried out, in addition fixing a vibrating element to the outlet tube. The vibrating element is a rotary motor (Precision Drive 4 mm, reference 304-101). It is operated at a voltage of 3 V.

Figure 8:
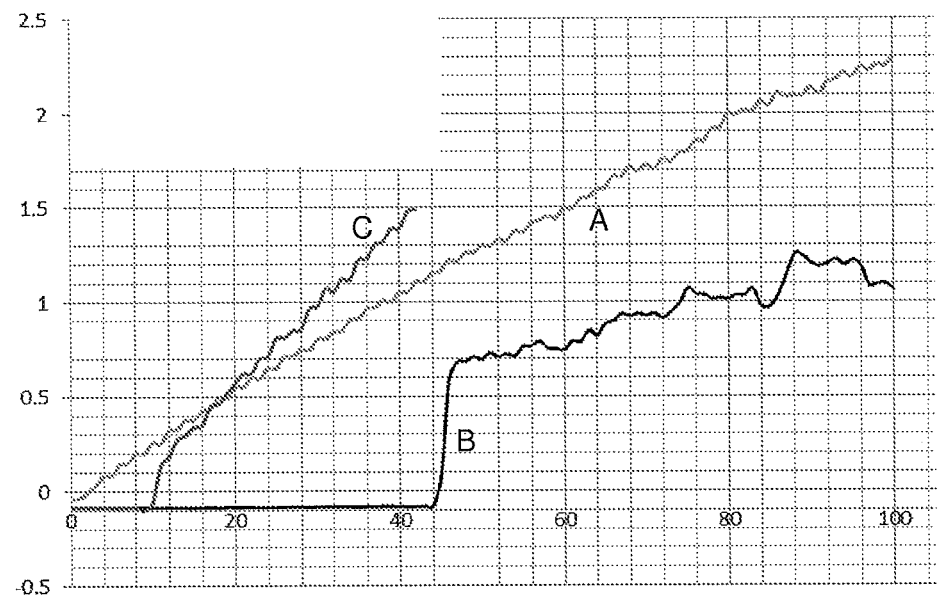
FIG. 8 shows the flow rate in microliters/min (on the Y-axis) as a function of the pressure in mbar (on the X-axis) in one embodiment of the invention (see example 4).

The change in the flow rate as a function of the pressure imposed is studied. The results can be seen in FIG. 8. Curve A is a measurement without magnetic particles. Curve B is a measurement with magnetic particles without vibrations. Curve C is a measurement with magnetic particles and with vibrations.

It is found that the presence of mechanical vibrations, by combating the tendency of the magnetic particles to aggregation, reduces the pressure necessary for obtaining a given flow rate, which increases the efficiency of the system.

Example 5—Selective Capture of Salmonella Bacteria in the Presence of *colibacilli*

A device according to FIG. 1 in example 1 is constructed, and controlled by a MAESFLO flow rate control system from the company Fluigent.

The channel is first of all loaded with 50 µg of magnetic balls in the same way as in example 3, except for the nature of the balls, which here carry anti-salmonella antibodies.

A suspension containing inactivated salmonellas marked by means of a green fluorescent marker, at saturation concentration divided by 1000, in an addition phosphate buffer of 0.1% BSA (bovine serum albumin), as well as *E. coli colibacilli* at the same concentration marked by a red fluorescent marker, is perfused in the chamber containing the magnetic balls, at a rate of 1 µL/min for 20 minutes. The system is next rinsed with buffer without bacteria.

After rinsing, photographs of the system are taken in the two red and green fluorescence channels. The capture ratio is evaluated as the ratio of the number of pixels having in the green a value greater than 3 times the background noise to the number of pixels having in the red a value greater than 3 times the background noise. This ratio, which is equal to 80±10, shows a good specificity of the system. Furthermore this ratio is in reality under-evaluated since the most abundant species captured (salmonellas) more frequently give rise to the superimposition of several bacteria in the same pixel, and therefore to an underestimation of the number of bacteria.

The invention claimed is:

1. A microfluidic system comprising:
    at least one channel for the flow of fluid having an inlet, an outlet and a longitudinal axis extending between the inlet and the outlet, said channel comprising a capture zone, and the cross section of the channel orthogonal to the longitudinal axis of the channel increasing in size in the capture zone, from the inlet towards the outlet of the channel; and
    a magnet, wherein the magnet is configured to apply a magnetic field having a decreasing intensity in the capture zone of the channel, from the inlet towards the outlet of the channel.

2. The system according to claim 1, wherein the magnetic field applied in the capture zone is parallel or forms an angle of less than 20° with respect to the longitudinal axis of the channel.

3. The system according to claim 1, wherein the equipment for applying the magnetic field comprises a magnet disposed outside the channel.

4. The system according to claim 1, wherein the capture zone of the channel comprises magnetic particles.

5. The system of claim 4, wherein the volume fraction of the magnetic particles in the capture zone of the channel is from 0.01 to 0.3.

6. The system according to claim 1, wherein the outlet of the channel is connected to a secondary conduit, the hydraulic resistance of which is greater than the hydraulic resistance of the channel.

7. The system according to claim 1, further comprising a pump, wherein the pump is configured to move fluid or effect the flow of fluid from the inlet to the outlet of the channel.

8. The system of claim 7, further comprising an oscillating device configured to generate oscillations of fluid in the channel.

9. The system according to claim 1, wherein the magnet is a permanent magnet, an electromagnet, or a combination thereof.

10. The system according to claim 7, wherein the pump is a microfabricated pump, an external pump, a microfluidic control pump, a syringe pump, peristaltic pump, a membrane pump, a piston pumps, a rotary pump, or a combination thereof.

11. The system according to claim 8, wherein the oscillating device is a sonic transducer, an ultrasonic transducer, a piezoelectric transducer, a motor having a vibrating element, a loudspeaker, or an oscillating piston.

* * * * *